United States Patent
Montgomery, III

(10) Patent No.: US 8,491,460 B1
(45) Date of Patent: Jul. 23, 2013

(54) METHOD AND APPARATUS FOR TREATING VAGINAL PROLAPSE

(71) Applicant: Joseph S. Montgomery, III, Cypress, TX (US)

(72) Inventor: Joseph S. Montgomery, III, Cypress, TX (US)

(*) Notice: Subject to any disclaimer, the term of this patent is extended or adjusted under 35 U.S.C. 154(b) by 0 days.

(21) Appl. No.: 13/715,797

(22) Filed: Dec. 14, 2012

(51) Int. Cl.
*A61F 2/00* (2006.01)

(52) U.S. Cl.
USPC .......................................................... 600/37

(58) Field of Classification Search
USPC .................. 600/29–31, 37; 606/139–158, 232
IPC ......................................................... A61F 2/00
See application file for complete search history.

(56) References Cited

U.S. PATENT DOCUMENTS

| | | | |
|---|---|---|---|
| 6,093,201 A * | 7/2000 | Cooper et al. ................ | 606/232 |
| 6,638,284 B1 | 10/2003 | Rousseau et al. | |
| 7,131,943 B2 | 11/2006 | Kammerer | |
| 7,285,086 B2 | 10/2007 | Smith et al. | |
| 7,500,945 B2 | 3/2009 | Cox et al. | |
| 7,601,118 B2 | 10/2009 | Smith et al. | |
| 7,628,155 B2 | 12/2009 | Carey | |
| 7,901,346 B2 | 3/2011 | Kovac et al. | |
| 7,985,173 B2 | 7/2011 | Jacquetin | |
| 8,057,382 B2 | 11/2011 | Thierfelder et al. | |
| 8,182,413 B2 | 5/2012 | Browning | |
| 8,201,559 B2 | 6/2012 | Carey | |
| 8,211,005 B2 | 7/2012 | Cox et al. | |
| 2002/0005204 A1 * | 1/2002 | Benderev et al. ............ | 128/898 |
| 2002/0099259 A1 * | 7/2002 | Anderson et al. ............. | 600/29 |
| 2002/0099260 A1 * | 7/2002 | Suslian et al. ................ | 600/30 |
| 2005/0004576 A1 * | 1/2005 | Benderev ..................... | 606/72 |
| 2005/0199249 A1 | 9/2005 | Karram | |
| 2005/0216042 A1 * | 9/2005 | Gertner ........................ | 606/151 |
| 2005/0283040 A1 * | 12/2005 | Greenhalgh ................. | 600/30 |
| 2007/0021649 A1 * | 1/2007 | Nowlin et al. ............... | 600/30 |
| 2008/0132754 A1 * | 6/2008 | Thierfelder et al. ......... | 600/37 |
| 2008/0234543 A1 | 9/2008 | Goldwasser | |
| 2011/0082331 A1 * | 4/2011 | Montpetit .................... | 600/37 |
| 2011/0105836 A1 | 5/2011 | Miller | |
| 2011/0313241 A1 | 12/2011 | Benderev | |

FOREIGN PATENT DOCUMENTS

WO         2007109508         9/2007

\* cited by examiner

*Primary Examiner* — Charles A Marmor, II
*Assistant Examiner* — Catherine E Burk
(74) *Attorney, Agent, or Firm* — Buskop Law Group, PC; Wendy Buskop

(57) ABSTRACT

A method and apparatus for restoring a prolapsed vagina within a patient pelvic cavity without insertion through the vaginal cavity and without attachment to the sacrum. The apparatus includes a plurality of tubular mesh grafts for insertion through a non-vaginal laparoscopic port wherein each tubular mesh graft has an internal end and an external end and installed surgical suture woven into the external end; and further wherein the internal end is attached to a vaginal apex and a surgical button for each tubular mesh graft, that is adapted to slide on installed surgical suture from a location external to the patient's body using one of a plurality of non-vaginal groin passageways until each surgical button can be secured adjacent the external end of each tubular mesh graft leaving the tubular mesh graft within the patient pelvic cavity supporting the prolapsed vagina.

2 Claims, 13 Drawing Sheets

FIGURE 1A

| | |
|---|---|
| CREATING A NON-VAGINAL UMBILICAL LAPAROSCOPIC PORT IN A PATIENT PELVIC CAVITY | 200 |
| CREATING A FIRST NON-VAGINAL LAPAROSCOPIC PORT LATERAL TO THE NON-VAGINAL UMBILICAL LAPAROSCOPIC PORT IN A PATIENT PELVIC CAVITY | 202 |
| CREATING A SECOND NON-VAGINAL LAPAROSCOPIC PORT LATERAL TO THE NON-VAGINAL UMBILICAL LAPAROSCOPIC PORT IN THE PATIENT PELVIC CAVITY AND OPPOSITE THE FIRST NON-VAGINAL LAPAROSCOPIC PORT | 204 |
| DISSECTING A SUBSTANTIAL AMOUNT (70 TO 100%) OF THE APEX PERITONEUM OFF A VAGINAL APEX IN THE PATIENT PELVIC CAVITY USING AT LEAST ONE LAPAROSCOPIC INSTRUMENT THROUGH THE FIRST NON-VAGINAL LAPAROSCOPIC PORT, THE SECOND NON-VAGINAL LAPAROSCOPIC PORT, OR COMBINATIONS THEREOF | 206 |
| INSERTING A BILATERAL TUBULAR MESH GRAFT THROUGH THE NON-VAGINAL UMBILICAL LAPAROSCOPIC PORT INTO A PATIENT PELVIC CAVITY | 208 |
| FORMING A NON-VAGINAL FIRST GROIN INCISION | 210 |
| TUNNELING WITH A FIRST CLAMP THROUGH THE NON-VAGINAL FIRST GROIN INCISION UNDER CAVITY PERITONEUM IN THE PATIENT PELVIC CAVITY TO A FIRST LOCATION PROXIMATE TO THE VAGINAL APEX THEREBY FORMING A NON-VAGINAL FIRST GROIN PASSAGEWAY FROM A FIRST LOCATION EXTERIOR OF THE PATIENT PELVIC CAVITY TO THE VAGINAL APEX | 212 |
| USING THE FIRST CLAMP, PULLING THE FIRST EXTERNAL END OF THE BILATERAL TUBULAR MESH GRAFT THROUGH THE NON-VAGINAL FIRST GROIN PASSAGEWAY THROUGH THE NON-VAGINAL FIRST GROIN INCISION TO EXTERIOR OF THE PATIENT PELVIC CAVITY, LEAVING THE CENTRAL PORTION AND SECOND EXTERNAL END OF THE BILATERAL TUBULAR MESH GRAFT IN BOTH THE PATIENT PELVIC CAVITY ADJACENT THE VAGINAL APEX AND THE NON-VAGINAL FIRST GROIN PASSAGEWAY | 214 |
| THREADING A FIRST SURGICAL BUTTON ONTO THE INSTALLED FIRST SURGICAL SUTURE OF THE BILATERAL TUBULAR MESH GRAFT | 216 |
| SLIDING THE FIRST SURGICAL BUTTON DOWN THE INSTALLED FIRST SURGICAL SUTURE UNTIL THE FIRST SURGICAL BUTTON ADJOINS THE FIRST EXTERNAL END OF THE BILATERAL TUBULAR MESH GRAFT | 218 |
| SECURING THE FIRST SURGICAL BUTTON TO THE FIRST EXTERNAL END OF THE BILATERAL TUBULAR MESH GRAFT USING THE ATTACHED FIRST SURGICAL SUTURE | 220 |
| GRASPING WITH ONE OF THE LAPAROSCOPIC INSTRUMENTS, THE SECOND EXTERNAL END OF THE BILATERAL TUBULAR MESH GRAFT AND PULLING THE SECOND EXTERNAL END UNTIL THE FIRST SURGICAL BUTTON RESTS ON THE FASCIA DISPOSED BETWEEN A CAVITY PERITONEUM AND SKIN OF THE PATIENT | 222 |
| FORMING A NON-VAGINAL SECOND GROIN INCISION | 224 |
| TUNNELING WITH A SECOND CLAMP THROUGH THE NON-VAGINAL SECOND GROIN INCISION UNDER THE CAVITY PERITONEUM IN THE PATIENT PELVIC CAVITY TO A SECOND LOCATION PROXIMATE TO THE VAGINAL APEX OPPOSITE THE FIRST LOCATION THEREBY FORMING A NON-VAGINAL SECOND GROIN PASSAGEWAY FROM A SECOND LOCATION EXTERIOR OF THE PATIENT PELVIC CAVITY TO THE VAGINAL APEX | 226 |

(1B)

(1A)

| | |
|---|---|
| USING THE SECOND CLAMP, PULLING THE SECOND EXTERNAL END OF THE BILATERAL TUBULAR MESH GRAFT THROUGH THE NON-VAGINAL SECOND GROIN PASSAGEWAY THROUGH THE NON-VAGINAL SECOND GROIN INCISION TO EXTERIOR OF THE PATIENT PELVIC CAVITY, LEAVING THE CENTRAL PORTION OF THE BILATERAL TUBULAR MESH GRAFT IN THE PATIENT PELVIC CAVITY ADJACENT THE VAGINAL APEX AND THE NON-VAGINAL SECOND GROIN PASSAGEWAY | 228 |
| THREADING A SECOND SURGICAL BUTTON ONTO THE INSTALLED SECOND SURGICAL SUTURE OF THE BILATERAL TUBULAR MESH GRAFT | 230 |
| SLIDING THE SECOND SURGICAL BUTTON DOWN THE INSTALLED SECOND SURGICAL SUTURE UNTIL THE SECOND SURGICAL BUTTON ADJOINS THE SECOND EXTERNAL END OF THE BILATERAL TUBULAR MESH GRAFT | 232 |
| SECURING THE SECOND SURGICAL BUTTON TO THE SECOND EXTERNAL END OF THE BILATERAL TUBULAR MESH GRAFT USING THE ATTACHED SECOND SURGICAL SUTURE | 234 |
| GRASPING WITH ONE OF THE LAPAROSCOPIC INSTRUMENTS, THE CENTRAL PORTION AND PULLING THE CENTRAL PORTION UNTIL THE SECOND SURGICAL BUTTON RESTS ON THE FASCIA DISPOSED BETWEEN THE CAVITY PERITONEUM AND SKIN OF THE PATIENT | 236 |
| ATTACHING THE CENTRAL PORTION TO THE VAGINAL APEX OF THE PROLAPSED VAGINA USING EXISTING SURGICAL SUTURING TECHNIQUES WITH AN IMBRICATING TYPE STITCH WITHOUT ADDING TENSION TO THE BILATERAL TUBULAR MESH GRAFT, ALLOWING THE BILATERAL TUBULAR MESH GRAFTS TO BIDIRECTIONALLY SUPPORT THE PROLAPSED VAGINA | 238 |

| | |
|---|---|
| CREATING A NON-VAGINAL UMBILICAL LAPAROSCOPIC PORT IN A PATIENT PELVIC CAVITY | 300 |
| CREATING A FIRST NON-VAGINAL LAPAROSCOPIC PORT LATERAL TO THE NON-VAGINAL UMBILICAL LAPAROSCOPIC PORT IN A PATIENT PELVIC CAVITY | 302 |
| CREATING A SECOND NON-VAGINAL LAPAROSCOPIC PORT LATERAL TO THE NON-VAGINAL UMBILICAL LAPAROSCOPIC PORT IN THE PATIENT PELVIC CAVITY AND OPPOSITE THE FIRST NON-VAGINAL LAPAROSCOPIC PORT | 304 |
| DISSECTING A SUBSTANTIAL AMOUNT (70 TO 100%) OF THE APEX PERITONEUM OFF A VAGINAL APEX IN THE PATIENT PELVIC CAVITY USING AT LEAST ONE LAPAROSCOPIC INSTRUMENT THROUGH THE FIRST NON-VAGINAL LAPAROSCOPIC PORT, THE SECOND NON-VAGINAL LAPAROSCOPIC PORT, OR COMBINATIONS THEREOF | 306 |
| INSERTING A FIRST TUBULAR MESH GRAFT THROUGH THE NON-VAGINAL UMBILICAL LAPAROSCOPIC PORT INTO A PATIENT PELVIC CAVITY, WHEREIN THE FIRST TUBULAR MESH GRAFT HAS A FIRST EXTERNAL END; A FIRST INTERNAL END; AN INSTALLED FIRST SURGICAL SUTURE ATTACHED TO AND EXTENDING FROM THE FIRST EXTERNAL END; FURTHER WHEREIN THE FIRST TUBULAR MESH GRAFT UNILATERALLY SUPPORTS THE PROLAPSED VAGINA | 308 |
| FORMING A NON-VAGINAL FIRST GROIN INCISION | 310 |
| TUNNELING WITH A FIRST CLAMP THROUGH THE NON-VAGINAL FIRST GROIN INCISION UNDER CAVITY PERITONEUM IN THE PATIENT PELVIC CAVITY TO A FIRST LOCATION PROXIMATE TO THE VAGINAL APEX THEREBY FORMING A NON-VAGINAL FIRST GROIN PASSAGEWAY FROM A FIRST LOCATION EXTERIOR OF THE PATIENT PELVIC CAVITY TO THE VAGINAL APEX | 312 |
| USING THE FIRST CLAMP, PULLING THE FIRST EXTERNAL END OF THE FIRST TUBULAR MESH GRAFT THROUGH THE NON-VAGINAL FIRST GROIN PASSAGEWAY THROUGH THE NON-VAGINAL FIRST GROIN INCISION TO EXTERIOR OF THE PATIENT PELVIC CAVITY, LEAVING THE FIRST INTERNAL END IN THE PATIENT PELVIC CAVITY ADJACENT THE VAGINAL APEX | 314 |
| THREADING A FIRST SURGICAL BUTTON ONTO THE INSTALLED FIRST SURGICAL SUTURE OF THE FIRST EXTERNAL END OF THE FIRST TUBULAR MESH GRAFT | 316 |
| SLIDING THE FIRST SURGICAL BUTTON DOWN THE INSTALLED FIRST SURGICAL SUTURE UNTIL THE FIRST SURGICAL BUTTON ADJOINS THE FIRST EXTERNAL END | 318 |
| SECURING THE FIRST SURGICAL BUTTON TO THE FIRST EXTERNAL END USING THE ATTACHED FIRST SURGICAL SUTURE | 320 |
| GRASPING WITH ONE OF THE LAPAROSCOPIC INSTRUMENTS, THE INTERNAL END OF THE FIRST TUBULAR MESH GRAFT AND PULLING THE GRAFT UNTIL THE EXTERNAL END WITH THE ATTACHED FIRST SURGICAL BUTTON RESTS ON THE FASCIA LAYER OF THE ABDOMINAL WALL DISPOSED BETWEEN A CAVITY PERITONEUM AND SKIN OF THE PATIENT | 322 |
| INSERTING A SECOND TUBULAR MESH GRAFT THROUGH THE NON-VAGINAL UMBILICAL LAPAROSCOPIC PORT INTO A PATIENT PELVIC CAVITY, WHEREIN THE SECOND TUBULAR MESH GRAFT HAS A SECOND EXTERNAL END; A SECOND INTERNAL END; AN INSTALLED SECOND SURGICAL SUTURE ATTACHED TO AND EXTENDING FROM THE SECOND EXTERNAL END; FURTHER WHEREIN THE SECOND TUBULAR MESH GRAFT UNILATERALLY SUPPORTS THE PROLAPSED VAGINA | 324 |

(2B)

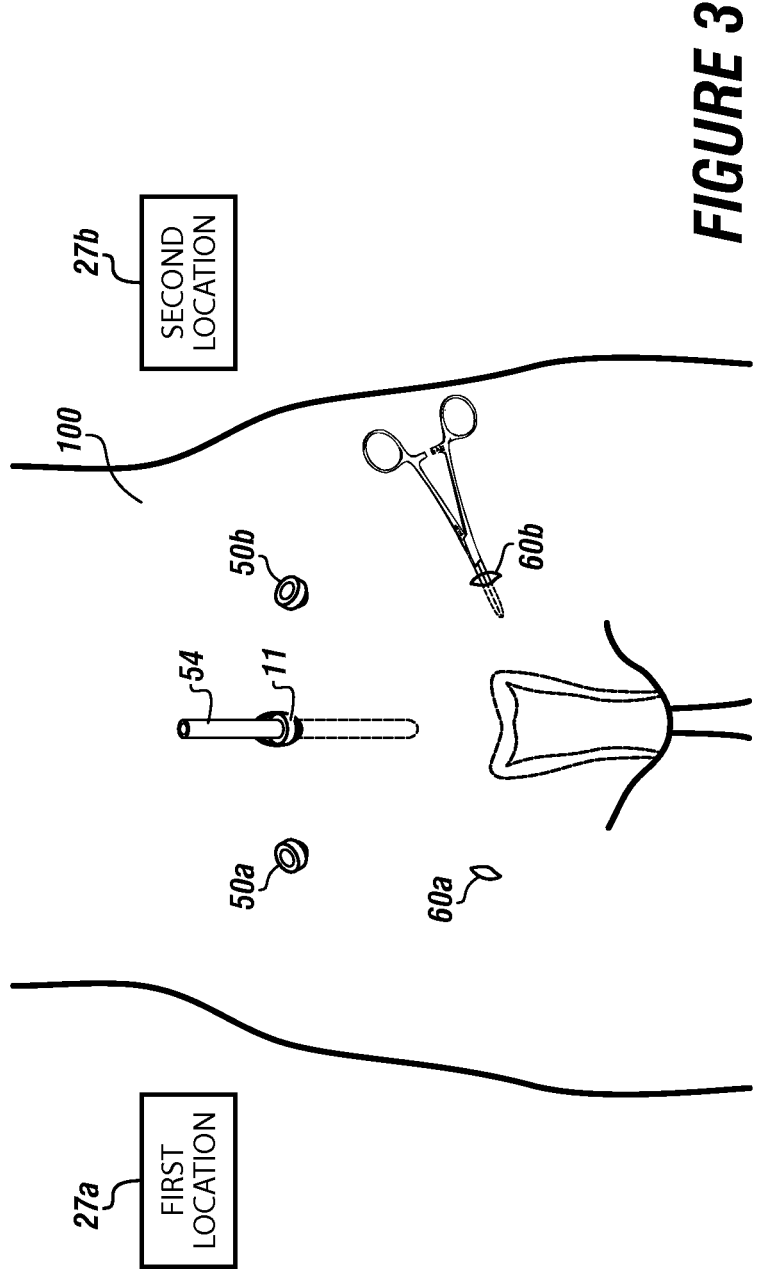

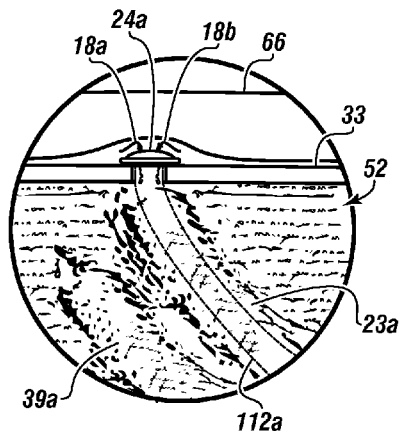
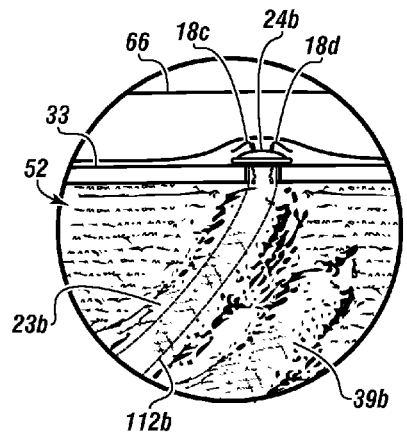
FIGURE 5A　　　　　　FIGURE 5B
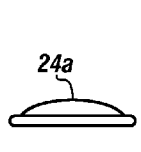
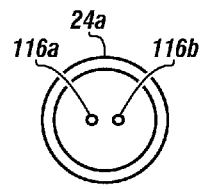
FIGURE 6A　　　FIGURE 6B
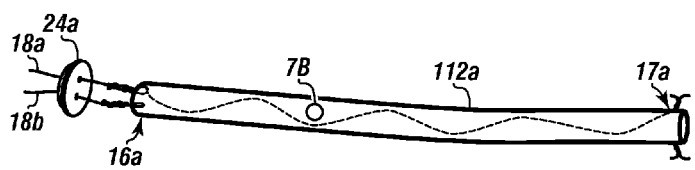
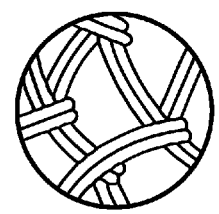
FIGURE 7A　　　　　FIGURE 7C
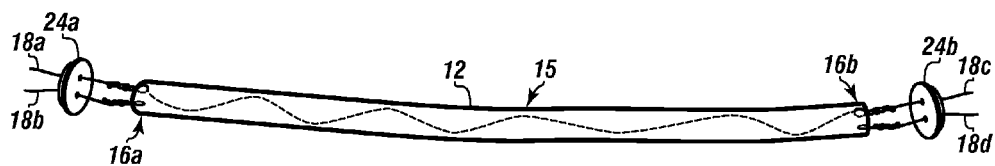
FIGURE 7B

METHOD AND APPARATUS FOR TREATING VAGINAL PROLAPSE

FIELD

The present embodiments generally relate to a method and apparatus for restoring a prolapsed vagina within a patient pelvic cavity.

BACKGROUND

A need exists for a method and apparatus for repairing vaginal prolapse without the risks involved with attaching mesh to a sacrum.

A need exits for a laparoscopic device along with a secondary gripping device to install tubular mesh grafts which have slidably attached surgical buttons to support the prolapsed vagina.

A further need exists for a long lasting repair providing support to the vaginal apex.

The present embodiments meet these needs.

BRIEF DESCRIPTION OF THE DRAWINGS

The detailed description will be better understood in conjunction with the accompanying drawings as follows:

FIGS. 1A-1B depict a sequence of steps usable in an embodiment of the method using a single piece bilateral graft.

FIGS. 2A-2B depict a sequence of steps usable in an embodiment of the method using a plurality of unilateral grafts.

FIG. 3 is top view of a patient with groin incisions usable in the method.

FIG. 5A depicts a first tubular mesh graft connected with a first surgical button atop the fascia layer of the abdominal wall on a first side.

FIG. 5B depicts a second tubular mesh graft connected with a second surgical button atop the fascia layer of the abdominal wall on a second side.

FIG. 6A is a side view of surgical button.

FIG. 6B is a top view of a surgical button.

FIG. 7A depicts a unilateral tubular mesh graft.

FIG. 7B depicts a bilateral one-piece tubular mesh graft.

FIG. 7C is a close-up view of the mesh used in FIGS. 7A and 7B.

Figure 2B:
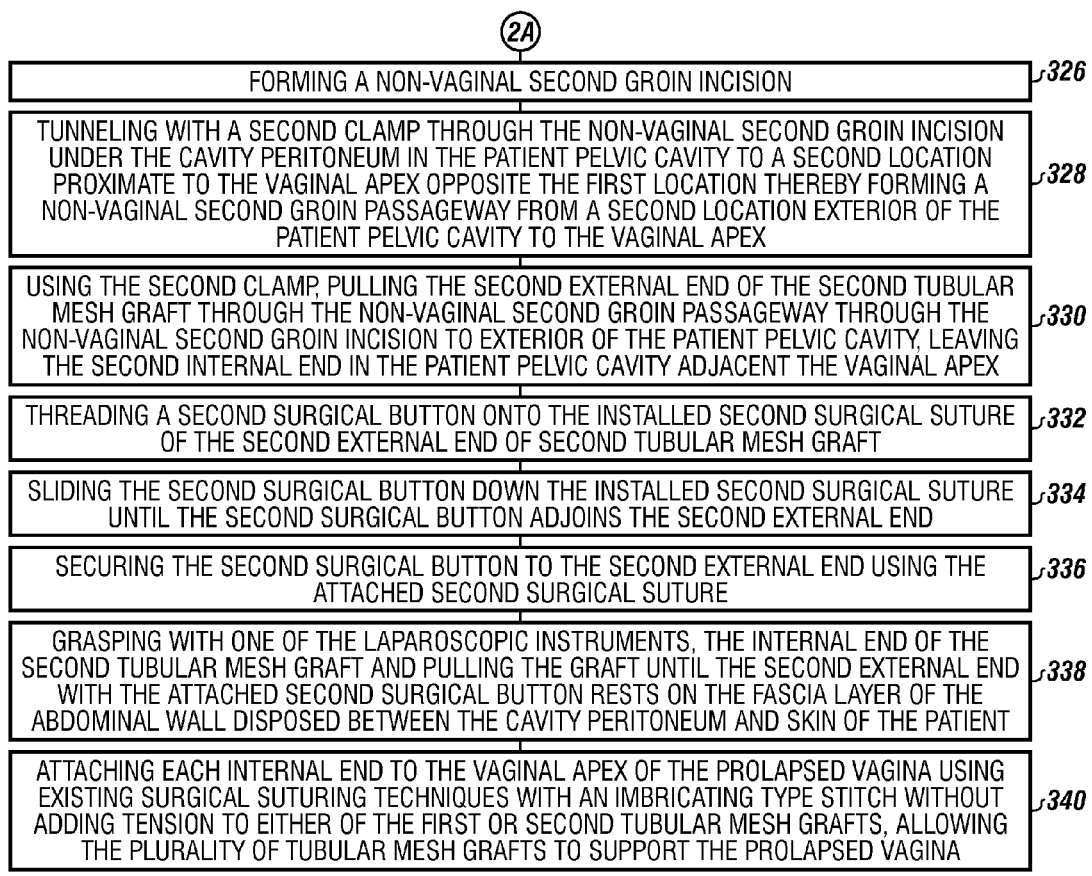

The present embodiments are detailed below with reference to the listed Figures.

DETAILED DESCRIPTION OF THE EMBODIMENTS

Before explaining the present apparatus in detail, it is to be understood that the apparatus is not limited to the particular embodiments and that it can be practiced or carried out in various ways.

The present embodiments generally relate to a system and method in the field of prolapsed vagina treatment.

More particularly, the present embodiments relate to a system with multiple components, and a method for surgically correcting vaginal prolapse.

This procedure provides long lasting support to the apex of the vagina. This method fixes a vagina that is prolapsing or "turning inside out". The method accomplishes this by providing supporting structures to allow support similar to the original supporting structures of the body.

The placement of support from an anterior and lateral direction provides support to the anterior vaginal wall and bladder. This method reduces the occurrence of bladder prolapse and urinary incontinence in the future for the patient. The lack of support for the anterior vaginal wall and bladder is a fault of existing repair methods that attach the vaginal apex to the sacrum or other more posterior attachment points.

The anterior and lateral approach avoids risks involved with attachment of the vagina to the sacrum or sacrospinous ligament as in currently used procedures. These risks include injuries to the urinary tract, nerves in the area and blood vessels.

The current embodiments can also provide a method that is less likely to lead to pain with sexual intercourse.

The anterior and lateral approach follows the path of the round ligaments which originally supports the uterus and the vagina. The uterus and vagina were never naturally attached to the sacral promontory. Attachment of the vagina to the sacrum as in current methods is not physiologically or anatomically correct, but no anterior and lateral mesh graft method has been heretofore developed.

This laparoscopic approach avoids implantation of the surgical mesh beneath the vaginal lining. Thus, complications of erosion of mesh through the vaginal lining are avoided. Such complication has been a well-known source of pain for many patients.

In one or more embodiments, the apparatus can include one or two tubular pre-cut mesh grafts using at least two surgical buttons connected by surgical sutures.

As is known to those skilled in the art, the treatment of vaginal wall prolapse has been hampered by high failure rates.

The main reasons for failure have been the inherent weakness of the tissue being re-approximated and the inability of the repaired tissue to withstand the forces applied by the abdominal cavity bearing down from above.

In the last decade, one major advance has been the addition of grafts to reinforce those repairs.

While this phenomenon has been gaining widespread acceptance, there lacks a consensus regarding how to affix the graft to the vagina to best maintain durability and vaginal caliber.

The most commonly accepted procedure for surgical treatment of pelvic organ prolapse is an abdominal sacrocolopopexy (ASC).

The procedure was originally described as being performed through an open incision, i.e., laparotomy, wherein one end of a wide graft was attached to the vagina with multiple sutures and the other end attached to the sacral promontory after opening the enclosing tissue layer known as the peritoneum.

The procedure has been refined over the years and has multiple subtle variations. It is acknowledged that the procedure, as described, has several limitations and, as such, the procedure is not utilized by all surgeons despite its overall level of success as compared to other treatments. For example, opening the peritoneum and sewing within the retroperitoneal space requires special skill and there is significant risk of bleeding. In addition, it is particularly challenging to apply the correct amount of tension to the graft needed to elevate the vagina and then fixate the graft at that tension.

Further, this approach has been associated with an increased risk of serious bowel complications, including potentially life threatening bowel obstruction. To avoid these complications, some surgeons have begun to attempt this procedure laparoscopically, at times employing known robotic techniques. However, this also creates a number of technical challenges as laparoscopic knot tying is a skill possessed by only a limited number of surgeons.

One alternative treatment approach for prolapse has been to introduce the mesh transvaginally. The evolution of transvaginal mesh procedures has produced several deployment devices to increase safety and make the procedures accessible to more surgeons.

There are numerous problems with introducing the mesh transvaginally, and many lawsuits have arisen due to problems associated with this type of treatment.

Some surgeons prefer to not introduce the mesh directly through the vagina due to potential inherent infectious and sexual complications associated with transvaginal introduction.

Accordingly, it has been desired to provide a device and method of treating vaginal prolapse that combines the ease of use of a mesh graft that is deployed laparoscopically.

The present invention with its enhancements to the shape of the graft and the method of attachment to an apex of the vagina provide increased safety and ease of use for surgeons.

The use of the surgical button allows for an easier install on the patient and eliminates the need to suture a graft to the sacrum.

The present embodiments were developed to support the vagina without the need for any tension during fixing of the tubular mesh grafts to the vaginal apex.

These enhancements thereby allow a greater number of patients to be treated using a minimally invasive prolapse treatment.

The present apparatus and method address the failure or unsatisfactory result from other method for repairing apical vaginal prolapse. Higher surgical risks occur with other methods. These embodiments provide a method that is a safer, more reliable, and the associated apparatus provides a tension free, more permanent repair for patients than known methods.

Furthermore, the apparatus can provide long lasting support to the vaginal apex.

The method is an anterior and lateral approach that provides support to the anterior vaginal wall and bladder.

The current method and apparatus avoid risks involved with attachment to the sacrum.

The present apparatus is used to follow a physiological path of round ligament which is an important support of the uterus and vagina.

The embodiments relate to apparatus for restoring a prolapsed vagina within a patient pelvic cavity.

The apparatus can include a tubular mesh graft for insertion through a formed laparoscopic port in a patient pelvic cavity such as by using a trocar and shaft.

In an embodiment, the tubular mesh graft can have an internal end and an external end and at least one installed surgical suture woven into the tubular mesh graft, and in another embodiment the tubular mesh graft can have a central portion and two external ends.

The external end of the first tubular mesh graft can be grasped by a clamp which penetrates from outside the patient body into the patient pelvic cavity. The clamp can be used to pull the external end of the first tubular mesh graft through the groin passageway formed in the patient pelvic cavity which was used for insertion of the clamp when using two unilateral tubular mesh grafts.

A surgical button can be slidably secured to the first tubular mesh graft, by being threaded onto a surgical suture. A surgical suture can be woven into the tubular mesh graft before the first tubular mesh graft was inserted into the patient body.

From outside of the patient's body the surgical button can be attached to the surgical suture. Then, the surgical button can be slid down the surgical suture to a location adjacent the external end of the first tubular mesh graft. The surgical button can then be tied down to the location using the surgical suture without penetrating the patient's tissue. The internal end of the first mesh graft can then be pulled back into the pelvic cavity until the button rests upon the fascia layer of the abdominal wall.

This process can then be repeated by making a second groin incision, inserting the clamp through the second groin incision, and creating a passageway beneath the peritoneal layer to a point near the vaginal apex.

A second tubular mesh graft with surgical suture already attached can be inserted into the patient body laparoscopically, such as with the trocar and sheath, as its external end is pulled upward and laterally through the second groin passageway and second groin incision.

A second surgical button can then be attached to the second internal end.

The internal end of the second mesh graft can then be pulled back into the pelvic cavity using a laparoscopic instrument until the second button rests on the fascia layer of the abdominal wall on the patient's opposite side.

The internal ends of both unilateral mesh grafts are then attached to the vaginal apex using existing laparoscopic suturing methods in an "imbricating" fashion.

Turning now to the Figures, FIGS. 1A and 1B depict a sequence of steps usable in an embodiment of the laparoscopic method for restoring a prolapsed vagina within a patient pelvic cavity using a single, one-piece, bilateral tubular mesh graft having two external ends and a central portion.

This is a laparoscopic method for restoring a prolapsed vagina within a patient pelvic cavity without attachment to the sacrum providing bidirectional support to the vagina.

As step 200, the method can include creating a non-vaginal umbilical laparoscopic port in a patient pelvic cavity.

As step 202, the method can include creating a first non-vaginal laparoscopic port lateral to the non-vaginal umbilical laparoscopic port in a patient pelvic cavity.

As step 204, the method can include creating a second non-vaginal laparoscopic port lateral to the non-vaginal umbilical laparoscopic port in the patient pelvic cavity and opposite the first non-vaginal laparoscopic port.

As step 206, the method can include dissecting a substantial amount (70% to 100%) of apex peritoneum off a vaginal apex in the patient pelvic cavity using at least one laparoscopic instrument through the first non-vaginal laparoscopic port, the second non-vaginal laparoscopic port, or combinations thereof.

As step 208, the method can include inserting a bilateral tubular mesh graft through the non-vaginal umbilical laparoscopic port into a patient pelvic cavity.

For this method, the bilateral tubular mesh graft can have a central portion; a first external end attached to the central portion, a second external end attached to the central portion opposite the first external end, an installed first surgical suture attached to and extending from the first external end, an installed second surgical suture attached to and extending from the second external end, and further the bilateral tubular mesh graft bidirectionally supports the prolapsed vagina.

As step 210, the method can include forming a non-vaginal first groin incision.

As step 212, the method can include tunneling with a first clamp through the non-vaginal first groin incision under cavity peritoneum in the patient pelvic cavity to a location proximate to the vaginal apex thereby forming a non-vaginal first groin passageway from a first location exterior of the patient pelvic cavity to the vaginal apex.

As step 214, the method can include using the first clamp, pulling the first external end of the bilateral tubular mesh graft through the non-vaginal first groin passageway through the non-vaginal first groin incision to exterior of the patient pelvic cavity, leaving the central portion and second external end of the bilateral tubular mesh graft in both the patient pelvic cavity adjacent the vaginal apex and the non-vaginal first groin passageway.

As step 216, the method can include threading a first surgical button onto the installed first surgical suture of the bilateral tubular mesh graft.

As step 218, the method can include sliding the first surgical button down the installed first surgical suture until the first surgical button adjoins the first external end of the bilateral tubular mesh graft.

As step 220, the method can include securing the first surgical button to the first external end of the bilateral tubular mesh graft using the attached first surgical suture.

As step 222, the method can include grasping with one of the laparoscopic instruments, the second external end of the bilateral tubular mesh graft and pulling the second external end until the first surgical button rests on the fascia layer of the abdominal wall disposed between a cavity peritoneum and skin of the patient.

As step 224, the method can include forming a non-vaginal second groin incision on the opposite side from the first groin incision.

As step 226, the method can include tunneling with a second clamp through the non-vaginal second groin incision under the cavity peritoneum in the patient pelvic cavity to a location proximate to the vaginal apex thereby forming a non-vaginal second groin passageway from a second location exterior of the patient pelvic cavity to the vaginal apex.

As step 228, the method can include using the second clamp, pulling the second external end of the bilateral tubular mesh graft through the non-vaginal second groin passageway through the non-vaginal second groin incision to exterior of the patient pelvic cavity, leaving the central portion of the bilateral tubular mesh graft in the patient pelvic cavity adjacent the vaginal apex and the non-vaginal second groin passageway.

As step 230, the method can include threading a second surgical button onto the installed second surgical suture of the bilateral tubular mesh graft.

As step 232, the method can include sliding the second surgical button down the installed second surgical suture until the second surgical button adjoins the second external end of the bilateral tubular mesh graft.

As step 234, the method can include securing the second surgical button to the second external end of the bilateral tubular mesh graft using the attached second surgical suture.

As step 236, the method can include grasping with one of the laparoscopic instruments, the central portion and pulling the central portion until the second surgical button rests on the fascia layer of the abdominal wall disposed between the cavity peritoneum and skin of the patient.

As step 238, the method can include attaching the central portion to the vaginal apex of the prolapsed vagina using existing surgical suturing techniques with an imbricating type stitch without adding tension to the bilateral tubular mesh graft, allowing the bilateral tubular mesh grafts to bidirectionally support the prolapsed vagina.

FIGS. 2A and 2B are a sequence of steps for an embodiment of the laparoscopic method for restoring a prolapsed vagina within a patient pelvic cavity using two unilateral tubular mesh grafts.

This is a laparoscopic method for restoring a prolapsed vagina within a patient pelvic cavity without attachment to the sacrum using a plurality of tubular mesh grafts.

As step 300, the method can include creating a non-vaginal umbilical laparoscopic port in a patient pelvic cavity.

As step 302, the method can include creating a first non-vaginal laparoscopic port lateral to the non-vaginal umbilical laparoscopic port in a patient pelvic cavity.

As step 304, the method can include creating a second non-vaginal laparoscopic port lateral to the non-vaginal umbilical laparoscopic port in the patient pelvic cavity and opposite the first non-vaginal laparoscopic port.

As step 306, the method can include dissecting a substantial amount (70% to 100%) of apex peritoneum off a vaginal apex in the patient pelvic cavity using at least one laparoscopic instrument through the first non-vaginal laparoscopic port, the second non-vaginal laparoscopic port, or combinations thereof.

As step 308, the method can include inserting a first tubular mesh graft through the non-vaginal umbilical laparoscopic port into a patient pelvic cavity, wherein the first tubular mesh graft has a first external end; a first internal end; an installed first surgical suture attached to and extending from the first external end; further wherein the first tubular mesh graft unilaterally supports the prolapsed vagina.

As step 310, the method can include forming a non-vaginal first groin incision.

As step 312, the method can include tunneling with a first clamp through the non-vaginal first groin incision under cavity peritoneum in the patient pelvic cavity to a location proximate to the vaginal apex thereby forming a non-vaginal first groin passageway from a first location exterior of the patient pelvic cavity to the vaginal apex.

As step 314, the method can include using the first clamp, pulling the first external end of the first tubular mesh graft through the non-vaginal first groin passageway through the non-vaginal first groin incision to exterior of the patient pelvic cavity, leaving the first internal end in the patient pelvic cavity adjacent the vaginal apex.

As step 316, the method can include threading a first surgical button onto the installed first surgical suture of the first external end of the first tubular mesh graft.

Step 318 of this method can include sliding the first surgical button down the installed first surgical suture until the first surgical button adjoins the first external end.

As step 320, the method can include securing the first surgical button to the first external end using the attached first surgical suture.

As step 322, the method can include grasping with one of the laparoscopic instruments, the internal end of the first tubular mesh graft and pulling the graft until the external end with the attached first surgical button rests on the fascia layer of the abdominal wall disposed between a cavity peritoneum and skin of the patient.

As step 324, the method can include inserting a second tubular mesh graft through the non-vaginal umbilical laparoscopic port into a patient pelvic cavity, wherein the second tubular mesh graft has a second external end; a second internal end; an installed second surgical suture attached to and extending from the second external end; further wherein the second tubular mesh graft unilaterally supports the prolapsed vagina.

As step 326, the method can include forming a non-vaginal second groin incision.

As step 328, the method can include tunneling with a second clamp through the non-vaginal second groin incision under the cavity peritoneum in the patient pelvic cavity to a first location proximate to the vaginal apex opposite the first location thereby forming a non-vaginal second groin passageway from a second location exterior of the patient pelvic cavity to the vaginal apex.

As step 330, the method can include using the second clamp, pulling the second external end of the second tubular mesh graft through the non-vaginal second groin passageway through the non-vaginal second groin incision to exterior of the patient pelvic cavity, leaving the second internal end in the patient pelvic cavity adjacent the vaginal apex.

As step 332, the method can include threading a second surgical button onto the installed second surgical suture of the second external end of second tubular mesh graft.

As step 334, the method can include sliding the second surgical button down the installed second surgical suture until the second surgical button adjoins the second external end.

As step 336, the method can include securing the second surgical button to the second external end using the attached second surgical suture.

As step 338, the method can include grasping with one of the laparoscopic instruments, the internal end of the second tubular mesh graft and pulling the graft until the second external end with the attached second surgical button rests on the fascia layer of the abdominal wall disposed between the cavity peritoneum and skin of the patient.

As step 340, the method can include attaching each internal end to the vaginal apex of the prolapsed vagina using existing surgical suturing techniques with an imbricating type stitch without adding tension to either of the first or second tubular mesh grafts, allowing the plurality of tubular mesh grafts to support the prolapsed vagina.

FIG. 3 is a top view of a patient 100 with groin incisions 60a and 60b which can be placed near the original insertion of the round ligaments through the inguinal ring.

Two additional laparoscopic ports can be formed, a first non-vaginal laparoscopic port 50a proximate to the non-vaginal umbilical laparoscopic port 11 and a second non-vaginal laparoscopic port 50b proximate to the non-vaginal umbilical laparoscopic port wherein all ports penetrate to the patient's pelvic cavity 13 shown in FIG. 4.

A laparoscopic instrument 54 can be inserted into each of the ports for implementation of the method, shown here inserted into the non-vaginal umbilical laparoscopic port 11.

A first location 27a external the patient pelvic cavity and a second location 27b external the patient pelvic cavity are also shown.

Figure 4A:
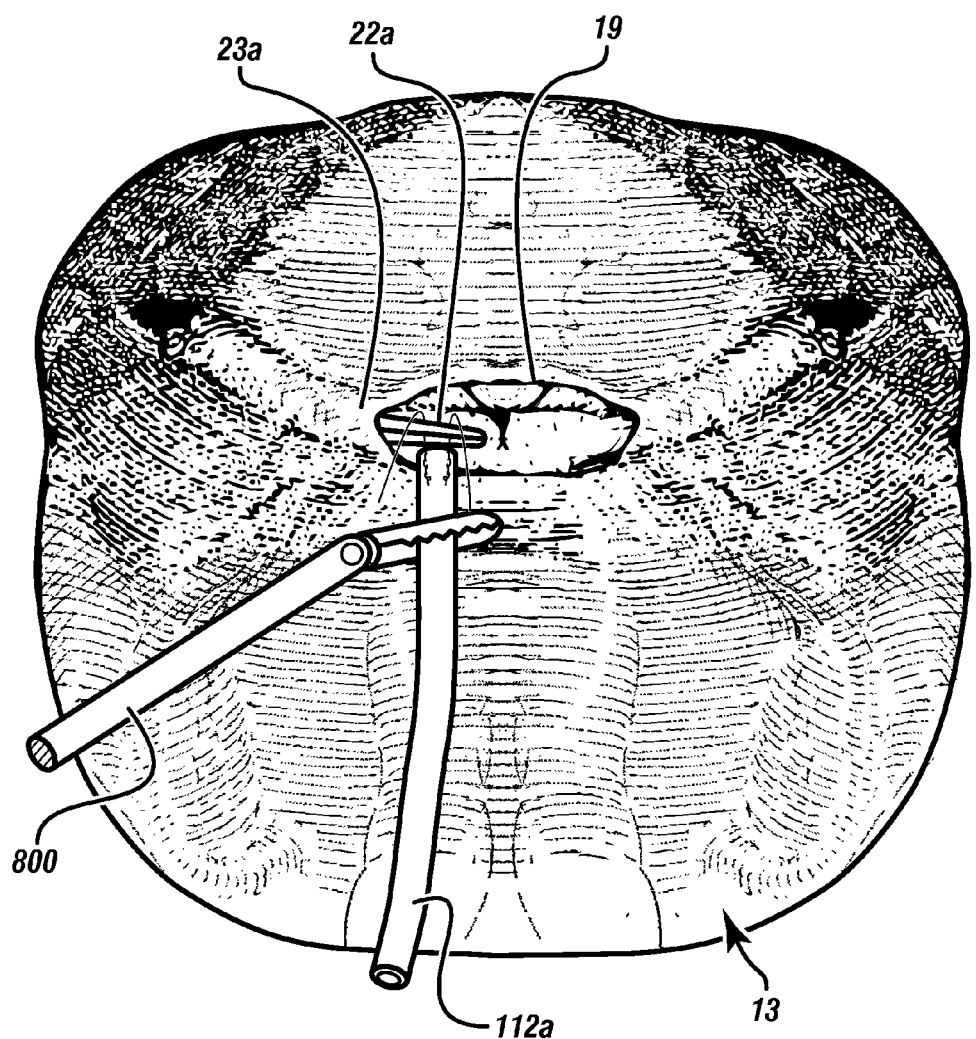
FIGS. 4A-4C depict a laparoscopic view of a mesh tubular graft installation using two unilateral tubular mesh grafts.
Figure 4B:
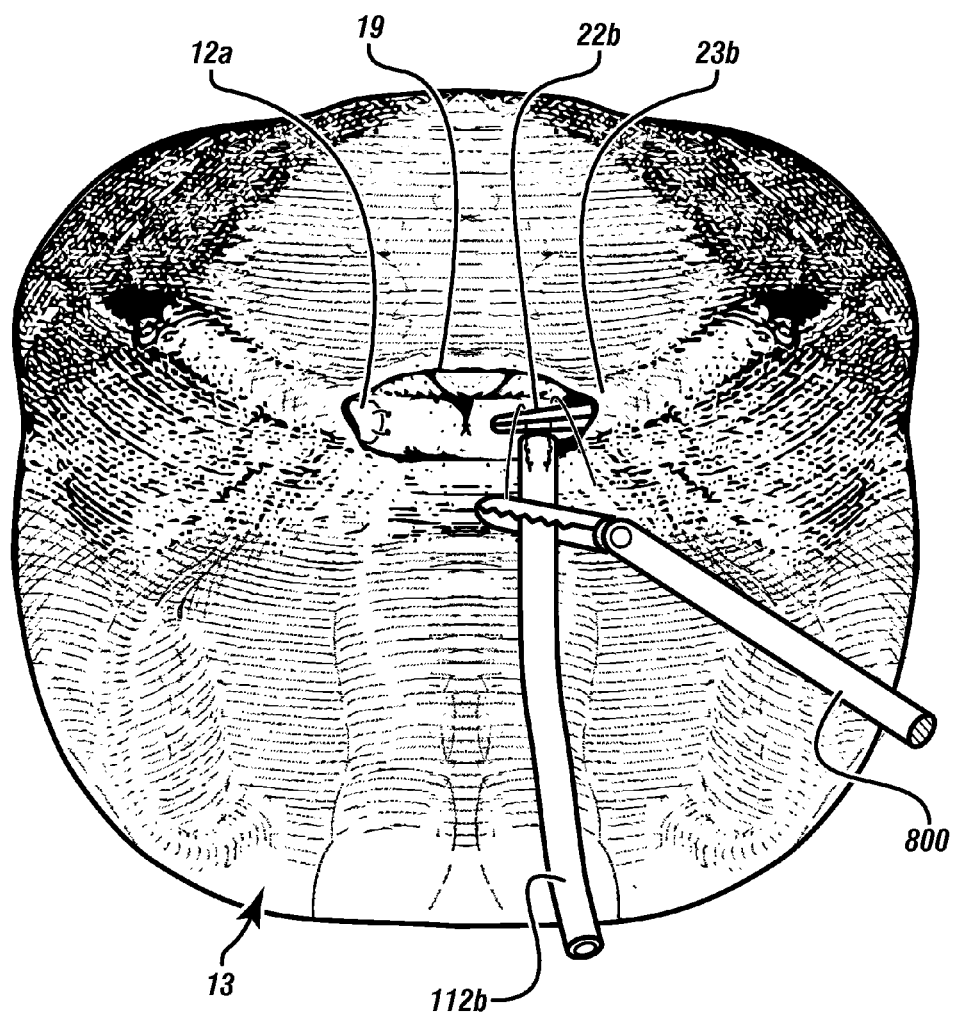
Figure 4C:
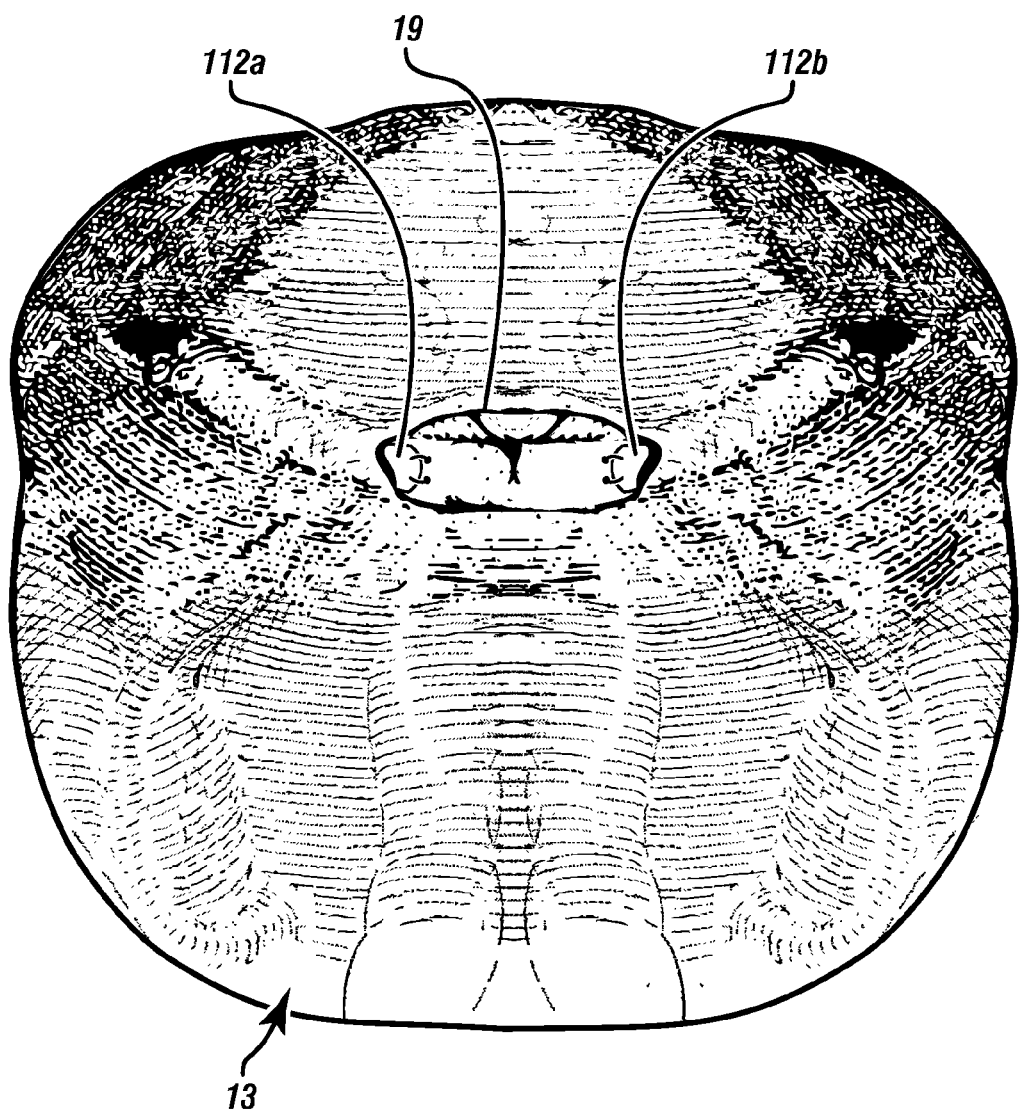

FIGS. 4A-4C depict a laparoscopic view of a two-piece unilateral mesh tubular graft installation.

The patient pelvic cavity 13 is shown after a non-vaginal first groin incision and a non-vaginal second groin incision have been made.

The first clamp 22a can tunnel through a first groin passageway 23a and the second clamp 22b can tunnel through a second groin passageway 23b.

The first clamp 22a can grasp an external end of a first unilateral tubular mesh graft 112a which is depicted having the attached surgical sutures 18a and 18b as shown in FIG. 5A.

The first unilateral tubular mesh graft 112a is depicted after being pushed down the non-vaginal umbilical laparoscopic port.

The second clamp 22b can grasp an external end of the second unilateral tubular mesh graft 12b which is depicted having the attached surgical sutures 18c and 18d as shown in FIG. 5B.

The first unilateral tubular mesh graft 112a and second unilateral tubular mesh graft 112b can be maneuvered inside the patient pelvic cavity using a guide clamp 800.

The vaginal apex 19 is also shown.

FIG. 4C is laparoscopic view of two installed unilateral tubular mesh grafts 112a and 112b in a patient pelvic cavity 13.

FIG. 5A depicts an external view of a first unilateral tubular mesh graft 112a that has been installed on the vaginal apex on a first internal end with a surgical button 24a installed on an external end. Surgical sutures 18a and 18c are depicted holding the surgical button 24a atop the fascia 33 between the vaginal apex and the skin 66 and within the cavity peritoneum and within the non-vaginal first groin passageway 23a.

A first tubular mesh graft 112a can be connected with a first surgical button atop the fascia layer of the abdominal wall on a first side.

The first tubular mesh graft 112a can be inserted through a first groin passageway 23a through an apex peritoneum 52. The first groin passageway 23a can be adjacent a first round ligament 39a.

A first surgical button 24a can be connected to the first graft 112a by an installed first surgical suture 18a and an installed second surgical suture 18b. The first surgical button 24a can set atop the fascia layer 33 of the abdominal wall and below the skin 66 on a first side.

FIG. 5B depicts a second tubular mesh graft connected with a second surgical button atop the fascia layer of the abdominal wall on a second side.

The second tubular mesh graft 112b can be inserted through a second groin passageway 23b through the apex peritoneum 52. The second groin passageway 23b can be adjacent a second round ligament 39b.

A second surgical button 24b can be connected to the second graft 112b by an installed third surgical suture 18c and an installed fourth surgical suture 18d. The second surgical button 24b can sit atop the fascia layer 33 of the abdominal wall and below the skin 66 on a second side.

FIG. 6A is a side view of surgical button 24a with a flat base and a raised middle.

FIG. 6B is a top view of a surgical button 24a with a first hole 116a and a second hole 116b centrally located to receive the surgical sutures.

FIG. 7A depicts a unilateral tubular mesh graft of which two are used in the first embodiment of the procedure detailed in FIGS. 2A and 2B.

The unilateral tubular mesh graft 112 can have a first internal end 17a and a first external end 16a.

The first unilateral tubular mesh graft 112a can include an installed first surgical suture 18a and an installed second surgical suture 18b attached to and extending from the first external end 16a.

A first surgical button 24a can be adapted to thread to the installed first surgical suture 18a and the installed second suture 18b from locations external to the patient.

The second unilateral tubular mesh graft can be identical to the first tubular mesh graft 112a.

FIG. 7B depicts a bilateral one-piece tubular mesh graft.

The one-piece bilateral tubular mesh graft 12 can have a first external end 16a and a second external end 16b. A center portion 15 can be located between the first external end 16a and the second external end 16b.

A first surgical button 24a can be adapted to thread to an installed first surgical suture 18a and an installed second surgical suture 18b from locations external to the patient.

A second surgical button 24b can be adapted to thread to an installed third surgical suture 18c and an installed fourth surgical suture 18d from locations external to the patient.

FIG. 7C is a close-up view of the mesh used in FIGS. 7A and 7B.

Figure 8A:
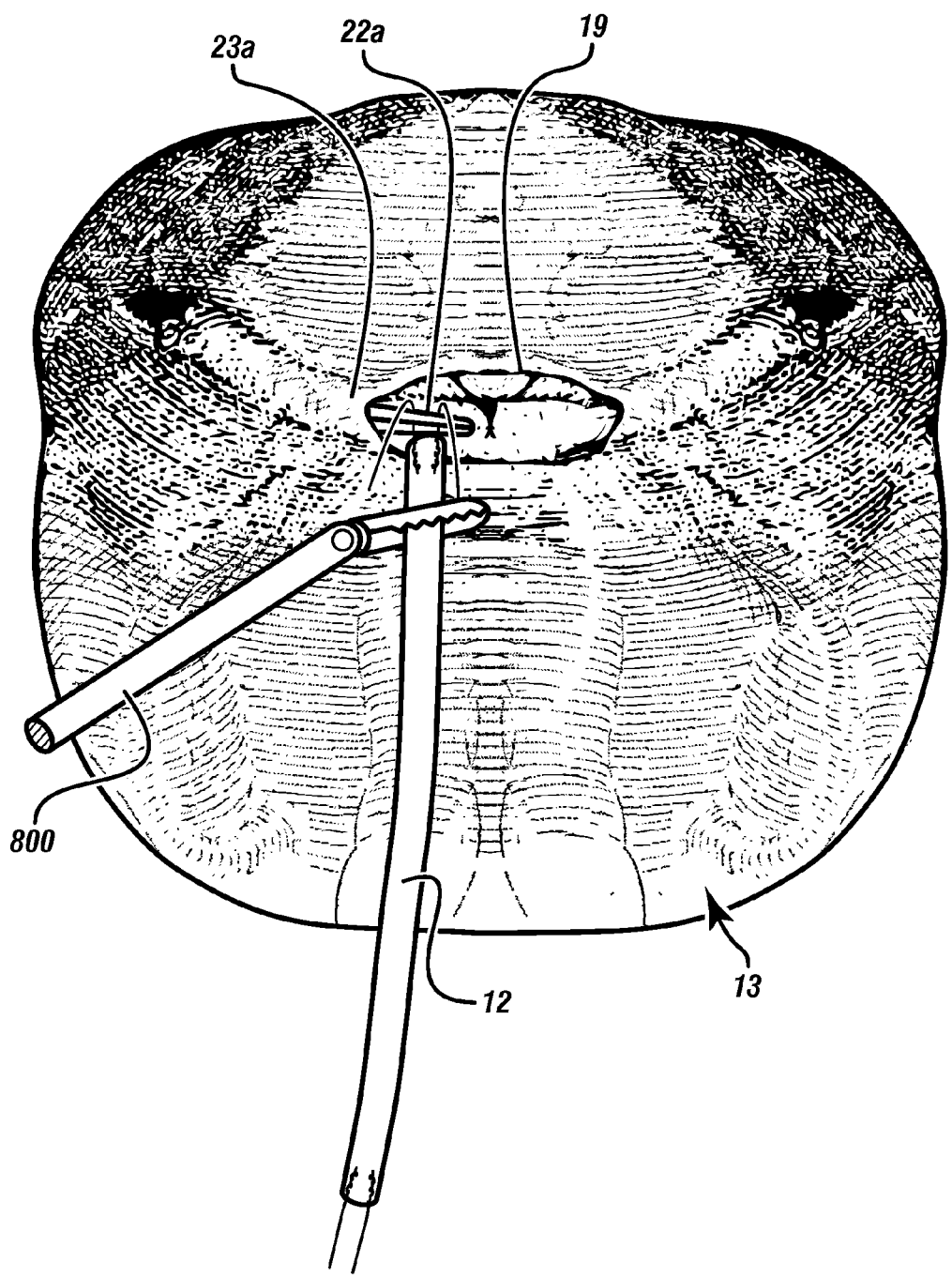
FIGS. 8A-8C depict a laparoscopic view of a mesh tubular graft installation using a bilateral one-piece tubular mesh graft with two external ends and a central portion.
Figure 8B:
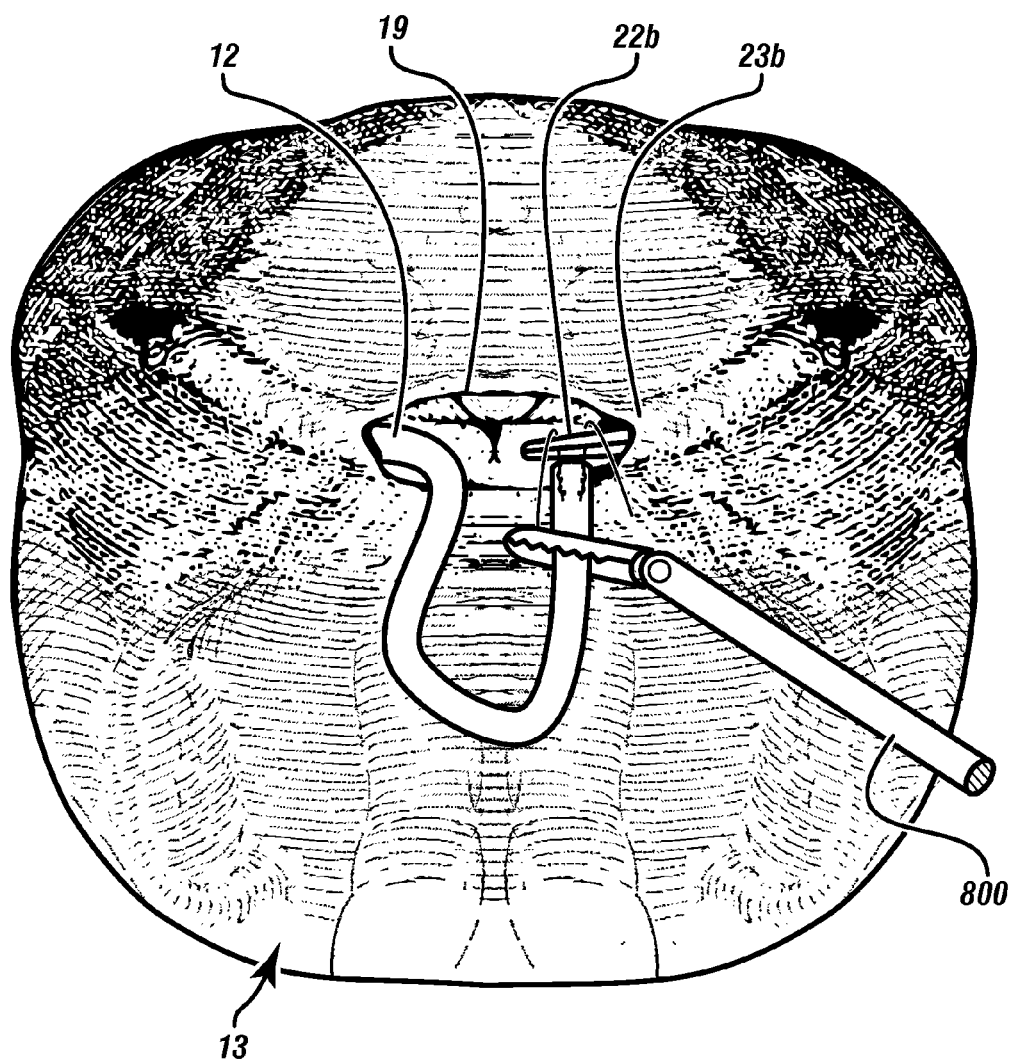
Figure 8C:
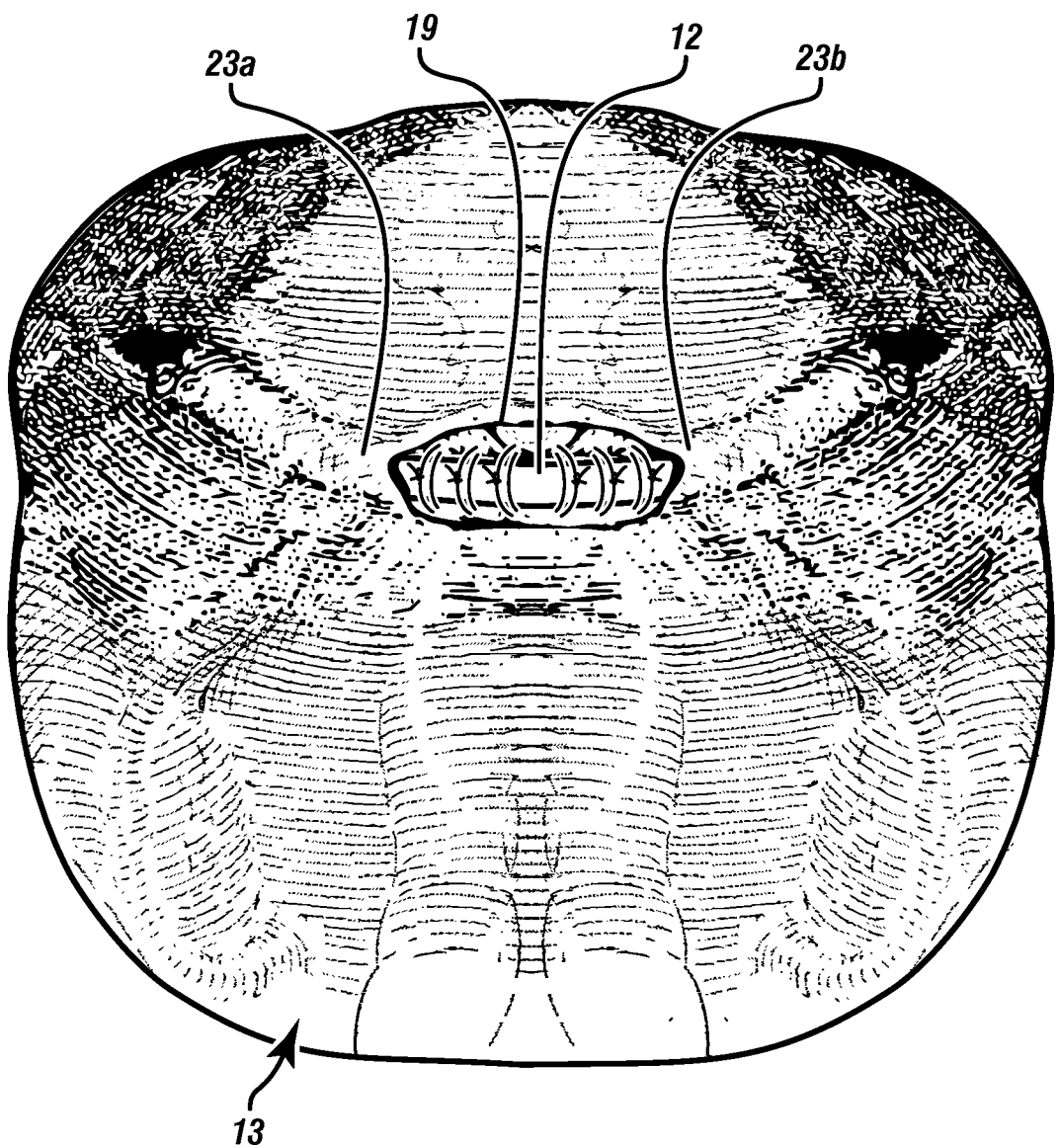

FIGS. 8A-8C depict a laparoscopic view of a mesh tubular graft installation using a bilateral one-piece tubular mesh graft with two external ends and a central portion.

Figure 8D:
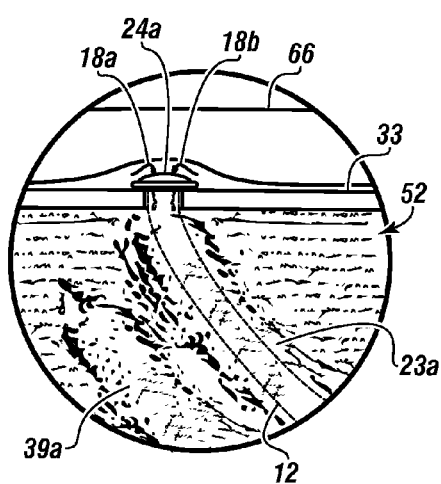
FIG. 8D is a side view of a surgical button atop the fascia layer of the abdominal wall on a first exterior end of the bilateral one-piece tubular mesh graft.
Figure 8E:
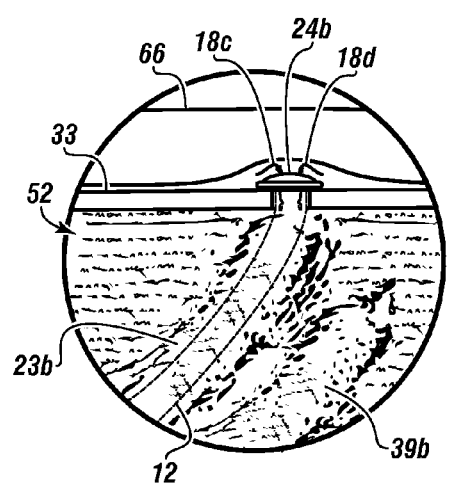
FIG. 8E is a side view of a surgical button atop the fascia layer of the abdominal wall on a second exterior end of the bilateral one-piece tubular mesh graft.

FIG. 8D is a side view of a surgical button atop the fascia layer of the abdominal wall on a first exterior end of the bilateral one-piece tubular mesh graft. FIG. 8E is a side view of a surgical button atop the fascia layer of the abdominal wall on a second exterior end of the bilateral one-piece tubular mesh graft.

Referring to FIG. 7B and FIGS. 8A-8E, a first clamp 22a can be used to tunnel the one-piece bilateral tubular mesh graft 12 through a non-vaginal first groin incision under a cavity peritoneum in the patient pelvic 13 cavity to a location proximate to the vaginal apex 19; thereby, forming a non-vaginal first groin passageway 23a from a first location exterior of the patient pelvic cavity 13 to an apex peritoneum 52 near the vaginal apex 19. The first groin passageway 23a can be adjacent a first round ligament 39a.

The first clamp 22a can grasp a first external end 16a of the one-piece bilateral tubular mesh graft 12.

A guide clamp 800 can be used to help guide the second external end 16b of the one-piece bilateral tubular mesh graft 12 as the first clamp 22a pulls the first external end 16a through the non-vaginal first groin passageway 23a.

The first clamp 22a can pull the first external end through the non-vaginal first groin passageway 23a through the non-vaginal first groin incision to exterior of the patient pelvic cavity, leaving the central portion 15 and second external end 16b of the bilateral tubular mesh graft 12 in both the patient pelvic cavity 13 adjacent the vaginal apex 19 and the non-vaginal first groin passageway 23a.

A first surgical 24a button can be threaded onto the first external end 16a using a first surgical suture 18a and a second surgical suture 18b. The first surgical 24a button can be moved down the installed first surgical suture until the first surgical button adjoins the first external end 16a of the bilateral tubular mesh graft 12.

The second clamp 22b can be used to tunnel through a non-vaginal second groin incision under the cavity peritoneum in the patient pelvic cavity 13 to a location proximate to the vaginal apex 19 thereby forming a non-vaginal second groin passageway 23b from a second location exterior of the patient pelvic cavity 13 to the vaginal apex 19.

The second clamp 22b can be used to grasp the second external end 16b of the bilateral tubular mesh graft 12 and pull the second external end 16b until the first surgical button 24a rests on the fascia layer 33 of the abdominal wall disposed between a cavity peritoneum and skin 66 of the patient.

The second external end 16b can be pulled through the non-vaginal second groin passageway 23b through the non-vaginal second groin incision 23b to exterior of the patient pelvic cavity, leaving the central portion 15 of the bilateral tubular mesh graft 12 in the patient pelvic cavity 13 adjacent the vaginal apex 19.

The second groin passageway 23b can be adjacent the second round ligament 39b.

A second surgical button 24b can be installed on a third surgical suture 18c and a fourth surgical suture 18d on the second exterior end 16b. The second surgical button can be moved down the surgical sutures until the second surgical button 24b adjoins the second external end 16b.

The center portion 15 can be grasped with the guide clamp 800 and pulled until the second surgical button rests on the fascia 33 disposed between the cavity peritoneum 52 and skin 66 of the patient.

The central portion 15 can be attached to the vaginal apex 19 of the prolapsed vagina using existing surgical suturing techniques with an imbricating type stitch without adding tension to the bilateral tubular mesh graft, allowing the bilateral tubular mesh graft to bidirectionally support the prolapsed vagina.

In an embodiment, the patient can be taken to an operating room, given a satisfactory anesthesia, prepped and draped in the usual manner.

Laparoscopy is carried out through an umbilical incision in the usual manner. An 11 millimeter umbilical port can be made.

Careful inspection with laparoscopy can then be carried out.

A first tubular mesh graft is introduced into the pelvic cavity through the umbilical port.

A first small incision can be made in the groin area near the inguinal ring.

A sarot clamp can then be used to perforate the fascia of the patient and to tunnel down below the peritoneum until a point is reached adjacent to the apex of the vagina.

There, the external end of the first tubular mesh graft can be brought up through the tunnel beneath the peritoneum, exiting at the groin incision.

A second tubular mesh graft can be introduced into the pelvic cavity through the umbilical port.

A second small incision can then be created through the skin opposite the first small incision.

Tunneling beneath the peritoneum can be carried out using a sarot clamp until a point is reached adjacent the vaginal apex.

At this point the second external end of the tubular mesh graft can be brought up through the second tunnel, exiting the second small groin incision.

A surgical button can be slid down each sutures of each tubular mesh graft to a location adjacent the external ends of each tubular mesh graft. These sutures can be tied securing the surgical buttons to each external end.

The tubular mesh grafts can then be pulled inwards into the patient until the surgical buttons each rest on fascia between skin and peritoneum.

An ENDOSTITCH™ device can then be utilized to suture the internal ends of each tubular mesh graft to the vaginal apex at the vaginal cuff using a permanent suture, which can be a coated polyester.

Approximately five sutures can be placed attaching the tubular mesh grafts to the upper vagina at the apex.

A good suspension can be achieved without tension being applied to the tubular mesh grafts and reasonable hemostasis is noted.

An adhesion prevention material can then be introduced through the laparoscopic port and placed over the operative field to prevent adhesions. An example of an adhesion prevention material can be INTERCEED™ made by Johnson & Johnson.

The adhesion prevention material can be fixed to the peritoneum by coagulating the adhesion prevention material to the peritoneum at various points. All smoke and gasses are evacuated.

The abdominal incisions can then be closed in the usual manner.

It should be noted that that apparatus and method corrects prolapse of the vagina or "turning inside out" of the vagina.

This method can be undertaken using laparoscopic surgery, rather than simply planting mesh beneath the vaginal lining from a vaginal approach.

This method avoids attachment of the vagina to sensitive structures such as the sacrum and sacrospinous ligament.

After establishing laparoscopy the tubular mesh graft can be introduced into the peritoneal cavity and placed in the lower abdomen. A retractor or similar instrument in the vagina can be used to push the prolapsed vagina apex inward. The apex of the vagina is cleared of adhesions and its peritoneal covering is exposed.

A small incision that is five to ten millimeters can be made in the groin area near the original attachment point of the round ligament to the abdominal wall. A long surgical clamp can be introduced through this incision and passed beneath the peritoneal lining to a point near the apex of the vagina, passing along the original path of the round ligament.

The clamp can then pierce through the peritoneum at a point near the vaginal apex.

The external end of the first graft can be grasped by the clamp and brought up through the tunneled passageway formed by the clamp and through the groin incision.

The surgical button can be attached to the external end with the sutures woven into the end of the graft. The graft can then be pulled into the peritoneal cavity until the surgical button is snug against the abdominal wall fascia.

The internal end of the graft, after trimming to adjust the length, can be sutured to the vaginal apex with imbricating or burying type stitches, using existing laparoscopic suturing technique.

The graft thus supports the vaginal apex from a lateral and anterior direction simultaneously.

A second graft can then be placed in the same manner on the opposite side to provide symmetrical support.

An adhesion barrier material can, at the surgeon's option, be placed over the surgical area to prevent adhesion formation.

The operation is complete and all instruments can be removed and the small incisions closed in a standard way.

The method prevents recurrences of vaginal prolapse.

Surgical mesh usable herein can include mesh grafts from American Medical Systems (AMS), C. R. Bard, Inc., ETHICON™, or similar surgical mesh.

Surgical suture usable herein includes suture made of braided polyester polypropylene, nylon, or a similar material.

In one or more embodiments the bilateral tubular mesh graft can comprise a woven polymeric material with a density of openings in the mesh ranging from 30 to 1000 openings per inch.

In one or more embodiments the woven polymeric material can be a woven material of flexible fibers.

In one or more embodiments the flexible fibers can be made from: a polypropylene homopolymer, a polypropylene copolymer, a polypropylene-polyethylene blend and combinations thereof.

In one or more embodiments, the bilateral tubular mesh graft can have a diameter from about 8 millimeters to about 10 millimeters.

In one or more embodiments, a second surgical suture can be connected to each external end of the bilateral tubular mesh graft.

In one or more embodiments, a surgical button can be made from: a crystalline polypropylene homopolymer, a polypropylene copolymer, a polypropylene-polyethylene blends, and combinations thereof.

In one or more embodiments, the surgical button can include: at least one centrally disposed hole, or more centrally disposed holes, such as a pair of holes, enabling the surgical suture to pass through centrally through the button using the hole allowing the surgical button to slide down the installed surgical suture to the external end of the bilateral tubular mesh graft.

In one or more embodiments, the surgical button can have a diameter from about 1 centimeter to about 1.5 centimeters, and a thickness from about 0.5 millimeters to about 3 millimeters.

In one or more embodiments, the bilateral tubular mesh graft can have a length from about 30 centimeters to about 35 centimeters.

In one or more embodiments, each surgical button can have a surgical mesh coating for improving adhesion to the fascia, such as polypropylene mesh.

In one or more embodiments, the surgical mesh coating can further have an antibiotic carrier, such as bacitracin.

In one or more embodiments, a non-stick coating can be disposed on at least a portion of each internal end to reduce formation of adhesions internally, such as using GORTEX™, INTERCEED™, or another adhesion barrier.

While these embodiments have been described with emphasis on the embodiments, it should be understood that within the scope of the appended claims, the embodiments might be practiced other than as specifically described herein.

What is claimed is:

1. A laparoscopic method for restoring a prolapsed vagina within a patient pelvic cavity without attachment to the sacrum, the method comprising:
   a. creating a non-vaginal umbilical laparoscopic port in a patient pelvic cavity;
   b. creating a first non-vaginal laparoscopic port lateral to the non-vaginal umbilical laparoscopic port in a patient pelvic cavity;
   c. creating a second non-vaginal laparoscopic port lateral to the non-vaginal umbilical laparoscopic port in the patient pelvic cavity and opposite the first non-vaginal laparoscopic port;
   d. dissecting a substantial amount of apex peritoneum off a vaginal apex in the patient pelvic cavity using at least one laparoscopic instrument through the first non-vaginal laparoscopic port, the second non-vaginal laparoscopic port, or combinations thereof;
   e. inserting a bilateral one-piece tubular mesh graft through the non-vaginal umbilical laparoscopic port into a patient pelvic cavity, wherein the bilateral tubular mesh graft comprises:
      (i) a central portion;
      (ii) a first external end attached to the central portion;
      (iii) a second external end attached to the central portion opposite the first external end;
      (iv) an installed first surgical suture attached to and extending from the first external end; and
      (v) an installed second surgical suture attached to and extending from the second external end; further wherein the bilateral tubular mesh graft bidirectionally supports the prolapsed vagina;
f. forming a non-vaginal first groin incision;
g. tunneling with a first clamp through the non-vaginal first groin incision under cavity peritoneum in the patient pelvic cavity to a location proximate to the vaginal apex thereby forming a non-vaginal first groin passageway from a first location exterior of the patient pelvic cavity to the vaginal apex;
h. using the first clamp, pulling the first external end of the bilateral tubular mesh graft through the non-vaginal first groin passageway through the non-vaginal first groin incision to exterior of the patient pelvic cavity, leaving the central portion in the patient pelvic cavity adjacent the vaginal apex, the non-vaginal first groin passageway, or combinations thereof;
i. threading a first surgical button onto the installed first surgical suture of the bilateral tubular mesh graft;
j. sliding the first surgical button down the installed first surgical suture until the first surgical button adjoins the first external end of the bilateral tubular mesh graft;
k. securing the first surgical button to the first external end of the bilateral tubular mesh graft using the installed first surgical suture;
l. grasping with one of the laparoscopic instruments, the second external end of the bilateral tubular mesh graft and pulling the second external end until the first surgical button rests on a fascia layer of an abdominal wall disposed between a cavity peritoneum and skin of the patient;
m. forming a non-vaginal second groin incision;
n. tunneling with a second clamp through the non-vaginal second groin incision under the cavity peritoneum in the patient pelvic cavity to a location proximate to the vaginal apex thereby forming a non-vaginal second groin passageway from a second location exterior of the patient pelvic cavity to the vaginal apex;
o. using the second clamp, pulling the second external end of the bilateral tubular mesh graft through the non-vaginal second groin passageway through the non-vaginal second groin incision to exterior of the patient pelvic cavity, leaving the central portion of the bilateral tubular mesh graft in the patient pelvic cavity adjacent the vaginal apex and the first external end in the non-vaginal first groin passageway;
p. threading a second surgical button onto the installed second surgical suture of the bilateral tubular mesh graft;
q. sliding the second surgical button down the installed second surgical suture until the second surgical button adjoins the second external end of the bilateral tubular mesh graft;
r. securing the second surgical button to the second external end of the bilateral tubular mesh graft using the attached second surgical suture;
s. grasping with one of the laparoscopic instruments, the central portion and pulling the central portion until the second surgical button rests on fascia disposed between the cavity peritoneum and skin of the patient; and
t. attaching the central portion to the vaginal apex of the prolapsed vagina using existing surgical suturing techniques with an imbricating type stitch without adding tension to the bilateral tubular mesh graft, allowing the bilateral tubular mesh graft to bidirectionally support the prolapsed vagina.

2. A laparoscopic method for restoring a prolapsed vagina within a patient pelvic cavity without attachment to the sacrum, the method comprising:

a. creating a non-vaginal umbilical laparoscopic port in a patient pelvic cavity;
b. creating a first non-vaginal laparoscopic port lateral to the non-vaginal umbilical laparoscopic port in a patient pelvic cavity;
c. creating a second non-vaginal laparoscopic port lateral to the non-vaginal umbilical laparoscopic port in the patient pelvic cavity and opposite the first non-vaginal laparoscopic port;
d. dissecting a substantial amount of apex peritoneum off a vaginal apex in the patient pelvic cavity using at least one laparoscopic instrument through the first non-vaginal laparoscopic port, the second non-vaginal laparoscopic port, or combinations thereof;
e. inserting a first unilateral tubular mesh graft through the non-vaginal umbilical laparoscopic port into a patient pelvic cavity, wherein the first tubular mesh graft comprises:
  (i) a first external end;
  (ii) a first internal end; and
  (iii) an installed first surgical suture attached to and extending from the first external end; further wherein the first tubular mesh graft unilaterally supports the prolapsed vagina;
f. forming a non-vaginal first groin incision;
g. tunneling with a first clamp through the non-vaginal first groin incision under cavity peritoneum in the patient pelvic cavity to a location proximate to the vaginal apex thereby forming a non-vaginal first groin passageway from a first location exterior of the patient pelvic cavity to the vaginal apex;
h. using the first clamp, pulling the first external end of the first tubular mesh graft through the non-vaginal first groin passageway through the non-vaginal first groin incision to exterior of the patient pelvic cavity, leaving the first internal end in the patient pelvic cavity adjacent the vaginal apex;
i. threading a first surgical button onto the installed first surgical suture of the first external end of the first tubular mesh graft;
j. sliding the first surgical button down the installed first surgical suture until the first surgical button adjoins the first external end;
k. securing the first surgical button to the first external end using the installed first surgical suture;
l. grasping with one of the laparoscopic instruments, the internal end of the first tubular mesh graft and pulling the first external end until the first surgical button rests on a fascia layer of an abdominal wall disposed between a cavity peritoneum and skin of the patient;
m. inserting a second tubular mesh graft through the non-vaginal umbilical laparoscopic port into a patient pelvic cavity, wherein the second tubular mesh graft comprises:
  (i) a second external end;
  (ii) a second internal end; and
  (iii) an installed second surgical suture attached to and extending from the second external end; further wherein the second tubular mesh graft unilaterally supports the prolapsed vagina;
n. forming a non-vaginal second groin incision;
o. tunneling with a second clamp through the non-vaginal second groin incision under the cavity peritoneum in the patient pelvic cavity to a location proximate to the vaginal apex thereby forming a non-vaginal second groin passageway from a second location exterior of the patient pelvic cavity to the vaginal apex;

p. using the second clamp, pulling the second external end of the second tubular mesh graft through the non-vaginal second groin passageway through the non-vaginal second groin incision to exterior of the patient pelvic cavity, leaving the second internal end in the patient pelvic cavity adjacent the vaginal apex;
q. threading a second surgical button onto the installed second surgical suture of the second external end of second tubular mesh graft;
r. sliding the second surgical button down the installed second surgical suture until the second surgical button adjoins the second external end;
s. securing the second surgical button to the second external end using the attached second surgical suture;
t. grasping with one of the laparoscopic instruments, the internal end of the second tubular mesh graft and pulling the second external end until the second surgical button rests on fascia disposed between the cavity peritoneum and skin of the patient; and
u. attaching each internal end to the vaginal apex of the prolapsed vagina using existing surgical suturing techniques with an imbricating type stitch without adding tension to either of the first or second tubular mesh grafts, allowing the plurality of tubular mesh grafts to support the prolapsed vagina.

* * * * *